US006183776B1

(12) United States Patent
Depui et al.

(10) Patent No.: US 6,183,776 B1
(45) Date of Patent: Feb. 6, 2001

(54) ORAL PHARMACEUTICAL DOSAGE FORMS COMPRISING A PROTON PUMP INHIBITOR AND AN ANTACID AGENT OR ALGINATE

(75) Inventors: Helene Depui, Göteborg; Agneta Hallgren, Mölndal, both of (SE)

(73) Assignee: Astra Aktiebolag, Sodertalje (SE)

( * ) Notice: Under 35 U.S.C. 154(b), the term of this patent shall be extended for 0 days.

(21) Appl. No.: 08/750,934

(22) PCT Filed: Dec. 20, 1996

(86) PCT No.: PCT/SE96/01737

§ 371 Date: Feb. 13, 1997

§ 102(e) Date: Feb. 13, 1997

(87) PCT Pub. No.: WO97/25066

PCT Pub. Date: Jul. 17, 1997

(30) Foreign Application Priority Data

Jan. 8, 1996 (SE) .................................................. 9600071

(51) Int. Cl.⁷ .............................. A61K 9/22; A61K 9/24; A61K 9/26; A61K 9/28
(52) U.S. Cl. ........................ 424/468; 424/469; 424/472; 424/474
(58) Field of Search ................................ 424/468, 473, 424/472, 469, 474

(56) References Cited

U.S. PATENT DOCUMENTS

| | | | |
|---|---|---|---|
| 4,786,505 | 11/1988 | Lovgren et al. | 424/468 |
| 5,036,057 | 7/1991 | Martin | 514/54 |
| 5,112,813 | 5/1992 | Luber et al. | 514/54 |
| 5,244,670 * | 9/1993 | Upson et al. | 424/439 |
| 5,447,918 | 9/1995 | McCullough | 514/53 |
| 5,447,923 | 9/1995 | Catrenich et al. | 514/147 |
| 5,753,265 | 5/1998 | Bergstrand et al. | 424/474 |
| 5,817,338 | 10/1998 | Bergstrand et al. | 424/468 |
| 5,824,339 * | 10/1998 | Shimizu et al. | 424/466 |

FOREIGN PATENT DOCUMENTS

| | | |
|---|---|---|
| 0008780 | 8/1979 | (EP) . |
| 0072021 | 8/1982 | (EP) . |
| 0080341 | 11/1982 | (EP) . |
| 0526862 | 2/1983 | (EP) . |
| 0108295 | 10/1983 | (EP) . |
| 0108504 | 10/1983 | (EP) . |
| 0111103 | 10/1983 | (EP) . |
| 0170752 | 12/1984 | (EP) . |
| 0247983 | 2/1987 | (EP) . |
| 0286085 | 10/1988 | (EP) . |
| 0338861 | 10/1989 | (EP) . |
| 0013566 | 1/1990 | (EP) . |

(List continued on next page.)

OTHER PUBLICATIONS

Takeuchi, K. et al. (1989) "Healing process . . . " Digestion 42 (4) :202–211.

Eriksson, S. (1995) "Omeprazole and $H_2$–receptor antagonists . . . " European J. of Gastroenterology and Hepatology 7:465.

(List continued on next page.)

Primary Examiner—James M. Spear
(74) Attorney, Agent, or Firm—White & Case LLP

(57) ABSTRACT

An oral pharmaceutical dosage form comprising an acid susceptible proton pump inhibitor and one or more antacid agents or an alginate in a fixed formulation, wherein the proton pump inhibitor is protected by an enteric coating layer and an optional separating layer in between the proton pump inhibitor and the enteric coating. The fixed formulation is in the form of multilayered tablets, sachets or multiple unit tableted dosage forms. The multiple unit dosage form is most preferred. The new fixed formulation is especially useful in the treatment of disorders associated with dyspepsia such as heartburn.

27 Claims, 1 Drawing Sheet

FOREIGN PATENT DOCUMENTS

| | | |
|---|---|---|
| 0365947 | 2/1990 | (EP) . |
| 0391518 | 2/1990 | (EP) . |
| 0541369 | 11/1992 | (EP) . |
| 0587220 | 8/1993 | (EP) . |
| 0648487 | 10/1994 | (EP) . |
| 0723777 | 7/1996 | (EP) . |
| 2066070 | 12/1980 | (GB) . |
| 2091097 | 11/1981 | (GB) . |
| 2132887 | 11/1983 | (GB) . |
| 2189698 | 4/1987 | (GB) . |
| 2222772 | 3/1990 | (GB) . |
| 2285989 | 1/1995 | (GB) . |
| 8501207 | 9/1984 | (WO) . |
| 8503436 | 2/1985 | (WO) . |
| 8702240 | 9/1986 | (WO) . |
| 9312772 | 12/1992 | (WO) . |
| 9403160 | 7/1993 | (WO) . |
| 9501795 | 1/1995 | (WO) . |
| 9510264 | 4/1995 | (WO) . |
| 9532720 | 12/1995 | (WO) . |
| 9602236 | 2/1996 | (WO) . |
| 9629055 | 9/1996 | (WO) . |
| 9501780 | 7/1997 | (WO) . |
| 9725066 | 7/1997 | (WO) . |
| 9823272 | 6/1998 | (WO) . |

OTHER PUBLICATIONS

Bate, C.M., "Reflux Symptom Relief with Omeprazole in Patients without Unequivocal Esophagitis", Alimentary Pharmacology & Therapeutics, vol. 10, No. 4 (1996), pp. 547–552.

Wan, L.S.C., "A Multiple–unit Tablet Formulation for Multi–layer Drug–coated Granules", S.T.P. Pharma Sciences, 4(5) (1994), pp. 336–342.

* cited by examiner

ORAL PHARMACEUTICAL DOSAGE FORMS COMPRISING A PROTON PUMP INHIBITOR AND AN ANTACID AGENT OR ALGINATE

This application is a 371 of PCT/SE96/01737 filed Dec. 20, 1996.

FIELD OF THE INVENTION

The present invention is related to new oral pharmaceutical preparations especially for use in the prevention and treatment of dyspeptic symptoms like upper abdominal pain/discomfort and heartburn. The present preparations comprise a combination of different gastric acid suppressing agents, such as an acid susceptible proton pump inhibitor and antacid agent(s) and/or an alginate in a new fixed unit dosage form, especially a tableted dosage form. Furthermore, the present invention refers to a method for the manufacture of such preparations and the use of such preparations in medicine, especially in the treatment of dyspeptic symtoms.

BACKGROUND OF THE INVENTION

Dyspepsia is a common disorders and patients are seeing both gastroenterologists and general practicians because of it. Heartburn is a symptom of dyspepsia, and it is estimated that 44% of Americans have heartburn at least monthly and some has to contact a doctor about the problem, but only around 25% of the patients are seeing the doctor because of their dyspepsia problem. Symtoms associated with dyspepsia symtom are for instance upper abdominal pain/discomform and heartburn, indigestion, sour stomach, heartburn and other gastrointestinal disorders including gastro oesophageal reflux. The wide diversity of symptoms and disease severity produced by gastro oesophageal reflux has led to the need for more individualized treatment strategies.

Therapeutic agents effective in the treatment of dyspepsia include gastric acid suppressing agents, such as $H_2$ receptor antagonists, proton pump inhibitors, other agents of interest are antacids/alginates and prokinetic agents. These agents can be distinguished by their mechanisms of action, safety profile, pharmacokinetics and indications. WO 95/017080 describes a composition for use in the treatment of for instance heartburn, the composition comprises a $H_2$ receptor antagonist, such as famotidine, and an alginate and optionally simethicone.

Antacid agents and alginates may be used alone in the treatment of heartburn. They have a short duration of action but are seen as inexpensive and safe. Antacid agents work locally through a neutralisation of gastric acid. Alginates further give some mechanical protection against reflux or gastric acid into the oesophagasus. The main advantages of antacid agents and alginates are, that they provide fast relief of symtoms. The main disadvantage of antacid agents and alginates is that, dosing has to be repeated frequently to keep the patients free of symtoms, further that antacids in many cases do not provide symtom resolution, i.e. complete relief of symtoms.

$H_2$ receptor antagonists are widely prescribed for reducing gastric acid secretion systemically. Proton pump inhibitors, such as omeprazole, are rapidly taking share from $H_2$ receptor antagonists. Omeprazole is known to offer significant gain over $H_2$ receptor antagonists in terms of symptom resolution, healing and prevention of relapse. Proton pump inhibitors provide symtom resolution, but normally not immediately.

Proton pump inhibitors have in clinical studies been proven to be very effective in providing symtom resolution (usually within 24–48 hours) in patients with dyspepsia associated with gastric ulcers, duodenal ulcers, reflux oesophagitis and gastro oesophageal reflux without oesophagitis. It is for instance established that omeprazole is superior to $H_2$ receptor antagonists regarding healing of gastroduodenal and oesophageal lesions as well as providing dyspeptic symtom resolution in these conditions, See Eriksson S., Euro Journ of Gastroenterology & Hepatology 1995, 7:465.

EP 338861 describes a solid pharmaceutical preparation of an antacid and excipients. It is proposed to use this preparation in combination with a proton pump inhibitor or any other substance inhibit gastric acid secretion. There is no suggestion to combine these substances in one fixed unit dosage form.

U.S. Pat. No. 5,244,670 describes an ingestible pharmaceutical composition comprising a substance selected from the group consisting of antacid agents, acid secretion prevention agents, bismuth-containing agents, and mixtures thereof, and the excipient 3-1-menthoxy propane 1,2-diol. There are no specific arrangements discussed in neither of these references, to solve the problem with one of the component being an acid susceptible proton pump inhibitor.

A combination therapy of a proton pump inhibitor and an antacid or an alginate would provide immediate symtom relief, provided by the local effect of the antacid agent or the alginate, combined with a long-lasting symtom resolution provided by the systemically acting proton pump inhibitor. Such a combination would be ideal for "on-demand treatment" of dyspepsia as well as for symtom resolution. The combination therapy comprising an acid suppressing agent, for instance a proton pump inhibitor, together with an antacid agent or an alginate could also be an alternative to each of them separately in case of failure. It is well known that patient compliance is a main factor in receiving good results in medical treatments. Administration of two or even more different tablets to the patient is not convenient or satisfactory to achieve the most optimal results. The present invention now provides new oral dosage forms comprising two or more active substances combined in one fixed unit dosage form, preferably a tablet.

Some gastric acid suppressing agents, such as proton pump inhibitors, are susceptible to degradation/transformation in acid reacting and neutral media. In respect of the stability properties, it is obvious that the one of the active substances being a proton pump inhibitor must be protected from contact with acidic gastric juice by an enteric coating layer. There are different enteric coating layered preparations of proton pump inhibitors described in the prior art, see for example U.S. Pat. No. 4,786,505 (AB Hässle) describing a preparation comprising omeprazole.

There are problems to produce a fixed unit dosage form comprising a rather high amount of active substance. Different active substances in the same preparation give further problems. Preparation of a multiple unit tableted dosage form arises specific problems when enteric coating layered pellets comprising an acid susceptible proton pump inhibitor as active substance are compressed into tablets. If the enteric coating layer does not withstand the compression of the pellets into a tablet the susceptible active substance will be destroyed upon administration by penetrating acidic gastric juice, i.e. the acid resistance of the enteric coating layer of the pellets will not be sufficient in the tablet after compression.

SUMMARY OF THE INVENTION

The present invention provides oral, fixed unit dosage forms, i.e. multiple unit tableted dosage forms, layered formulations comprising an enteric coating layered tablet core, multilayered tablets or a sachet filled with more than one pharmaceutically active compound. The active compounds present in the dosage form are preferably an acid susceptible proton pump inhibitor and antacid agents. Alternatively, in some of the formulations the antacid agents may be replaced by an alginate. These new dosage forms will simplify the regimen and improve the patient compliance.

DETAILED DESCRIPTION OF THE INVENTION

One object of the invention is to provide an oral, multiple unit tableted dosage form comprising an acid susceptible proton pump inhibitor in the form of individually enteric coating layered units together with one or more antacid agents in the form of a powder or granules compressed into a tablet. The enteric coating layer(s) covering the individual units of the acid susceptible proton pump inhibitor has properties such that the compression of the units into a tablet does not significantly affect the acid resistance of the individually enteric coating layered units. Furthermore, the multiple unit tableted dosage form provides a good stability to the active substances during long-term storage.

A further object of the invention is to provide a multiple unit tableted dosage form, which is divisible and easy to handle. Such a multiple unit tableted dosage form comprising enteric coating layered pellets of a proton pump inhibitor and antacid agent(s) also may be dispersed in a slightly acidic aqueous liquid and can be given to patients with swallowing disorders and in pediatrics. Such a suspension of dispersed units/pellets of appropriate size can be used for oral administration and also for feeding through a nasogastric tube.

Another object of the invention is to provide a tablet preparation comprising a proton pump inhibitor in admixture with tablet excipients in a tablet core and a separate layer surrounding the tablet core, which layer comprises one or more antacid agent(s) in admixture with pharmaceutical excipients compressed onto the tablet core. The tablet core is enteric coating layered before the surrounding layer comprising the antacid agents is applied. Optionally a separating layer is applied on the tablet core before the core is enteric coating layered.

Alternatively, the prepared tablet is sectioned in separate layers, each one comprising different active substances. One of the layers comprises the proton pump inhibitor in the form of enteric coating layered pellets in admixture with pharmaceutical excipients and the other layer(s) comprises(-e) the antacid agent(s)/alginate, respectively in admixture with pharmaceutical excipients. Optionally the two layers are separated by a separating layer to prevent tacking between the two layers.

Figure 1:
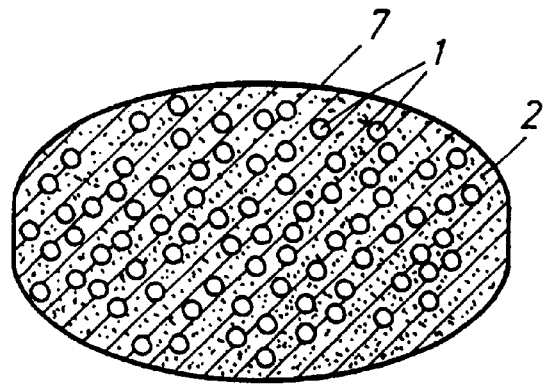
FIG. 1 illustrates a cross-section of a multiple unit tableted dosage form comprising an acid susceptible proton pump inhibitor in the form of enteric coating layered pellets (1) in admixture with antacid agent(s) and pharmaceutical excipients(2). Optionally, the tablet is covered by a film-coating layer, i.e. tablet coat (7).

The new fixed unit dosage forms comprise as active substances one gastric acid suppressing agent, such as an acid susceptible proton pump inhibitor, and antacid agent(s)/alginate. Alternatively, the proton pump inhibitor in the form of enteric coating layered pellets may be mixed with an alginate and optionally pharmaceutical excipients to be administred in a sachet intended for oral administration after dispersion in a sligthly acidic aqueous solution. The new fixed dosage form is preferably in the form of a multiple unit tableted dosage form containing enteric coating layered units comprising the active substance being an acid susceptible proton pump inhibitor and granules comprising the other active substance(s), i.e. the antacid agent(s) as shown in FIG. 1.

The antacid agent(s) may preferably be formulated in preparations intended for instant release. Alternatively, the components may be formulated in an effervescent formulation.

The different therapeutically active components used in the dosage forms are defined below.

Active Substances

The gastric acid suppressing agent is preferably an acid susceptible proton pump inhibitor. Such proton pump inhibitors are for example compounds of the general formula I

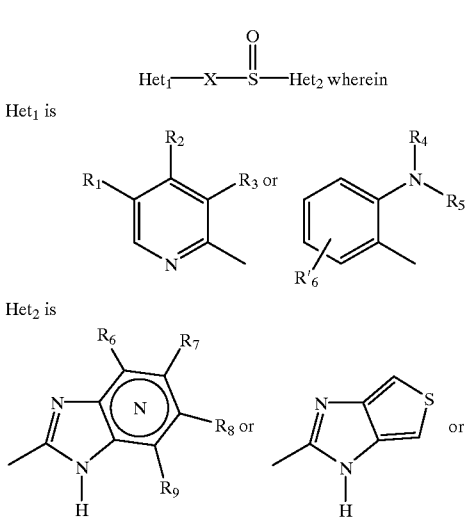

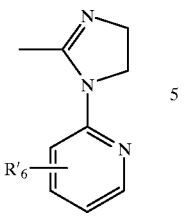

X =

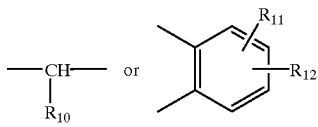

wherein

N in the benzimidazole moiety means that one of the carbon atoms substituted by $R_6$–$R_9$ optionally may be exchanged for a nitrogen atom without any substituents;

$R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

$R_4$ and $R_5$ are the same or different and selected from hydrogen, alkyl and aralkyl;

$R_6'$ is hydrogen, halogen, trifluoromethyl, alkyl and alkoxy;

$R_6$–$R_9$ are the same or different and selected from hydrogen, alkyl, alkoxy, halogen, halo-alkoxy, alkylcarbonyl, alkoxycarbonyl, oxazolyl, trifluoroalkyl, or adjacent groups $R_6$–$R_9$ form ring structures which may be further substituted;

$R_{10}$ is hydrogen or forms an alkylene chain together with $R_3$ and $R_{11}$ and $R_{12}$ are the same or different and selected from hydrogen, halogen or alkyl, alkyl groups, alkoxy groups and moities thereof, they may be branched or straight $C_1$–$C_9$-chains or comprise cyclic alkyl groups, such as cycloalkylalkyl.

Examples of proton pump inhibitors according to formula I are

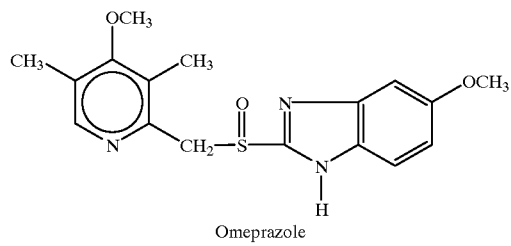

Omeprazole

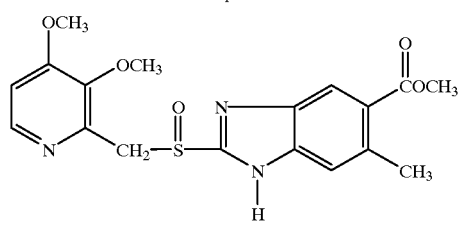

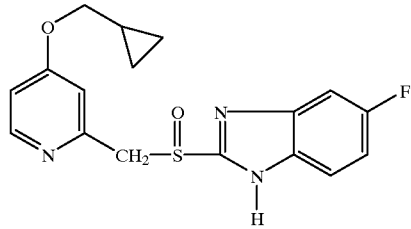

Lansoprazole

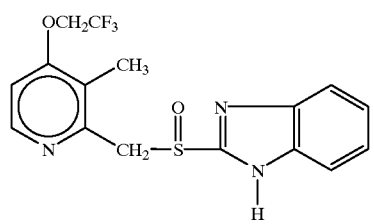

Pantoprazole

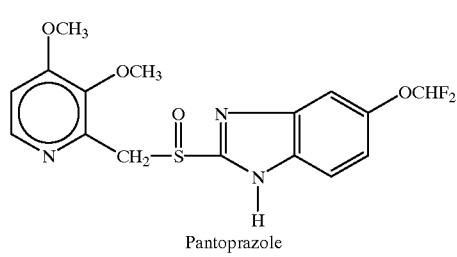

Pariprazole

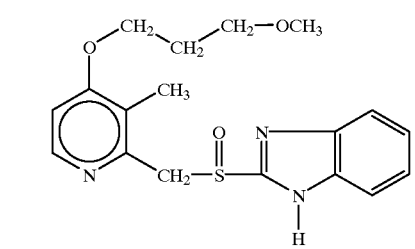

Leminoprazole

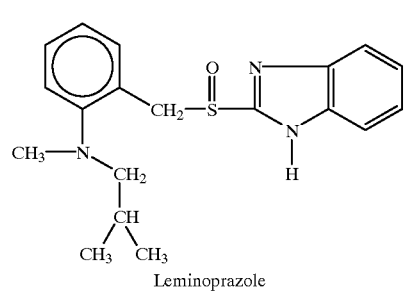

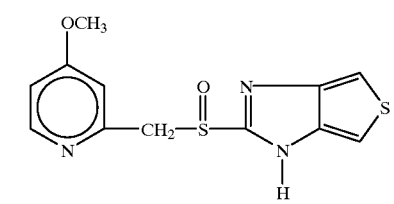

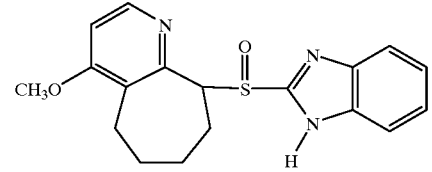

-continued

[chemical structures]

The proton pump inhibitors used in the dosage forms of the invention may be used in neutral form or in the form of an alkaline salt, such as for instance the $Mg^{2+}$ $Ca^{2+}$ $Na^+$, $K^+$ or $Li^+$ salts, preferably the $Mg^{2+}$ salts. Further where applicable, the compounds listed above may be used in racemic form or in the form of a substantially pure enantiomer thereof, or alkaline salts of the single enantiomers.

Suitable proton pump inhibitors are for example disclosed in EP-A1-0005129, EP-A1-174 726, EP-A1-166 287, GB 2 163 747 and WO90/06925, WO91/19711, WO91/19712, and further especially suitable compounds are described in WO95/01977 and WO094/27988.

The gastric acid suppressing agent is preferably an acid susceptible proton pump inhibitor but $H_2$ receptor antagonists such as ranitidine, cimetidine or famotidine may be used in the pharmaceutical compositions with an alginate as proposed in WO 95/017080 or together with antacid agent (s).

A wide variety of antacid agent(s) and/or alginates may be used in combination with a suitable proton pump inhibitor in the fixed unit dosage form according to the present invention. Such antacid agents include for example aluminium hydroxide, calcium carbonate, magnesium hydroxide, magnesium carbonate and aluminium magnesium hydroxide carbonate (hydrotalcit) taken alone or in combinations with each other. The alginates may be an alginate selected from alginic acid or sodium alginate or other pharmaceutically acceptable alginate salts, hydrates, esters etc. Especially preferred antacid agents are magnesium or calcium based antacid agents and aluminium hydroxide/magnesium carbonate complex. Suitable antacid agents are for instance described in U.S. Pat. No. 5,409,709.

The preferred multiple unit tableted dosage form comprising a proton pump inhibitor in the form of a racemat, an alkaline salt or one of its single enantiomers in combination with antacid agent(s), is characterized in the following way. Individually enteric coating layered units (small beads, granules or pellets) containing the acid susceptible proton pump inhibitor and optionally containing alkaline reacting substances, are mixed with the antacid(s) and conventionally tablet excipients. The antacid(s) and tablet excipients may be dry mixed or wet-mixed into granules. The mixture of enteric coating layered units, antacid agent(s) and optionally excipients are compressed into the multiple unit tableted dosage forms. With the expression "individual units" is meant small beads, granules or pellets, in the following referred to as pellets of the proton pump inhibitor.

The compaction process (compression) for formulating the multiple unit tableted dosage form must not significantly affect the acid resistance of the enteric coating layered pellets. In other words the mechanical properties, such as the flexibility and hardness as well as the thickness of the enteric coating layer(s), must secure that the requirements on enteric coated articles in the United States Pharmacopeia are accomplished in that the acid resistance does not decrease more than 10% during the compression of the pellets into tablets.

The acid resistance is defined as the amount of proton pump inhibitor in the tablets or pellets after being exposed to simulated gastric fluid USP, or to 0,1 M HCl (aq) relative to that of unexposed tablets and pellets, respectively. The test is accomplished in the following way. Individual tablets or pellets are exposed to simulated gastric fluid of a temperature of 37° C. The tablets disintegrate rapidly and release the enteric coating layered pellets to the medium. After two hours the enteric coating layered pellets are removed and analyzed for content of the proton pump inhibitor using High Performance Liquid Chromatography (HPLC).

Further specific components used in the fixed unit dosage forms of the present invention are defined below.

Core Material—for Enteric Coating Layered Pellets Comprising a Proton Pump Inhibitor The core material for the individually enteric coating layered pellets can be constituted according to different principles. Seeds layered with the proton pump inhibitor, optionally mixed with alkaline substances, can be used as the core material for the further processing.

The seeds which are to be layered with the proton pump inhibitor can be water insoluble seeds comprising different oxides, celluloses, organic polymers and other materials, alone or in mixtures or water-soluble seeds comprising different inorganic salts, sugars, non-pareils and other materials, alone or in mixtures. Further, the seeds may comprise the proton pump inhibitor in the form of crystals, agglomerates, compacts etc. The size of the seeds is not essential for the present invention but may vary between approximately 0.1 and 2 mm. The seeds layered with the proton pump inhibitor are produced either by powder or solution/suspension layering using for instance granulation or spray coating layering equipment.

Before the seeds are layered, the proton pump inhibitor may be mixed with further components. Such components can be binders, surfactants fillers, disintegrating agents, alkaline additives or other and/or pharmaceutically acceptable ingredients alone or in mixtures. The binders are for example polymers such as hydroxypropyl methylcellulose (HPMC), hydroxypropyl-cellulose (HPC), carboxymethylcellulose sodium, polyvinyl pyrrolidone (PVP), sugars, starches or other pharmaceutically acceptable substances with cohesive properties. Suitable surfactants are found in the groups of pharmaceutically acceptable non-ionic or ionic surfactants such as for instance sodium lauryl sulfate.

Alternatively, the proton pump inhibitor optionally mixed with alkaline substances and further mixed with suitable constituents can be formulated into a core material. Said core material may be produced by extrusion/spheronization, balling or compression utilizing conventional process equipment. The size of the formulated core material is approximately between 0.1 and 4 mm and preferably between 0.1 and 2 mm. The manufactured core material can further be layered with additional ingredients comprising the proton pump inhibitor and/or be used for further processing.

The proton pump inhibitor is mixed with pharmaceutical constituents to obtain preferred handling and processing properties and a suitable concentration of the substance in the final mixture. Pharmaceutical constituents such as fillers, binders, lubricants, disintegrating agents, surfactants and other pharmaceutically acceptable additives.

Further, the proton pump inhibitor may also be mixed with an alkaline, pharmaceutically acceptable substance (or substances). Such substances can be chosen among, but are not restricted to substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16}CO_3.4H_2O)$, $MgO.Al_2O_3.2SiO_2.nH_2O$ or similar compounds; organic pH-buffering substances such as trihydroxymethyl-aminomethane, basic amino acids and their salts or other similar, pharmaceutically acceptable pH-buffering substances.

Alternatively, the aforementioned core material can be prepared by using spray drying or spray congealing technique.

Enteric Coating Layer(s)

Before applying the enteric coating layer(s) onto the core material in the form of individual pellets or tablets, the pellets or tablets may optionally be covered with one or more separating layer(s) comprising pharmaceutical excipients optionally including alkaline compounds such as pH-buffering compounds. This/these separating layer(s), separate(s) the core material from the outer layers being enteric coating layer(s). The separating layer(s) protecting the proton pump inhibitor should be water soluble or rapidly disintegrating in water.

The separating layer(s) can be applied to the core material by coating or layering procedures in suitable equipments such as coating pan, coating granulator or in a fluidized bed apparatus using water and/or organic solvents for the coating process. As an alternative the separating layer(s) can be applied to the core material by using powder coating technique. The materials for the separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethyl-cellulose, hydroxypropyl methyl cellulose, carboxymethylcellulose sodium and others, used alone or in mixtures. Additives such as plasticizers, colorants, pigments, fillers anti-tacking and anti-static agents, such as for instance magnesium stearate, titanium dioxide, talc and other additives may also be included into the separating layer(s).

When the optional separating layer, is applied to the core material it may constitute a variable thickness. The maximum thickness of the separating layer(s) is normally only limited by processing conditions. The separating layer may serve as a diffusion barrier and may act as a pH-buffering zone. The pH-buffering properties of the separating layer(s) can be further strengthened by introducing into the layer(s) substances chosen from a group of compounds usually used in antacid formulations such as, for instance, magnesium oxide, hydroxide or carbonate, aluminium or calcium hydroxide, carbonate or silicate; composite aluminium/ magnesium compounds such as, for instance $Al_2O_3.6MgO.CO_2.12H_2O$, $(Mg_6Al_2(OH)_{16}CO_3.4H_2O)$, $MgO.Al_2O_3.2SiO_2.nH_2O$, aluminium hydroxide/so bicarbonate coprecipitate or similar compounds; or other pharmaceutically acceptable pH-buffering compounds such as, for instance the sodium, potassium, calcium, magnesium and aluminium salts of phosphoric, carbonic, citric or other suitable, weak, inorganic or organic acids; or suitable organic bases, including basic amino acids and salts thereof. Talc or other compounds may be added to increase the thickness of the layer(s) and thereby strenghten the diffusion barrier. The optionally applied separating layer(s) is not essential for the invention. However, the separating layer(s) may improve the chemical stability of the active substance and/or the physical properties of the novel multiple unit tableted dosage form.

Alternatively, the separating layer may be formed in situ by a reaction between an enteric coating polymer layer applied on the core material an alkaline reacting compound in the core material. Thus, the separating layer formed comprises a salt formed between the enteric coating layer polymer(s) and an alkaline reacting compound which is in the position to form a salt.

Figure 2:
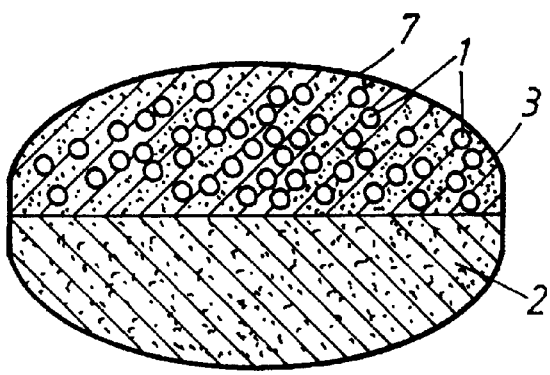
FIG. 2 illustrates a cross-section of a tablet with two separate layers, one of which comprising enteric coating layered pellets of an acid susceptible proton pump inhibitor (1) in admixture with excipients (3) and the other layer comprising a mixture of pharmaceutical excipients and an antacid agent(s) or an alginate (2). Optionally the layers are separated by an anti-tacking layer. Further the tablet is optionally covered by a filmcoating layer (7).
Figure 3:
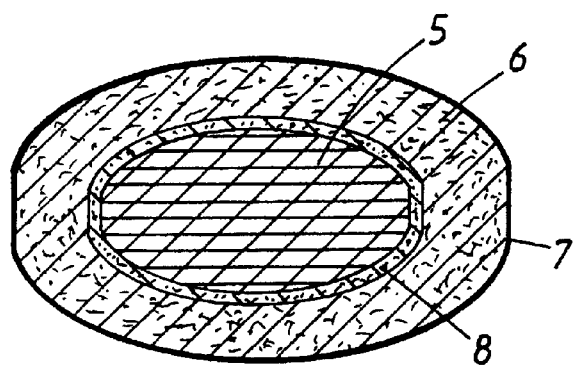
FIG. 3 illustrates a cross-section of a tablet comprising a mixture of pharmaceutical excipients and an acid susceptible proton pump inhibitor in the tablet core (5) surrounded by of an enteric coating layer (8) optionally with a separating layer applied in between the tablet core and the enteric coating layer and upon the enteric coating layer a layer of the antacid agent(s) in admixture with pharmaceutical excipients 6). Optionally, the tablet is covered by a filmcoating layer (7).

The separating layer may also be used to separate two different layers of a tablet, as described in FIG. 2.

One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers one or more, separately or in combination, of the following can be used, e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s).

The enteric coating layers may contain pharmaceutically acceptable plasticizers to obtain the desired mechanical properties, such as flexibility and hardness of the enteric coating layers. Such plasticizers are for instance, but not restricted to triacetin, citric acid esters, phthalic acid esters, dibutyl sebacate, cetyl alcohol, polyethylene glycols, polysorbates or other plasticizers.

The amount of plasticizer is optimized for each enteric coating layer formula, in relation to selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that the acid resistance of the pellets covered with enteric coating layer(s) does not decrease significantly during compression of pellets into tablets. The amount of plasticizer is usually above 10% by weight of the enteric coating layer polymer(s), preferably 15–50% and more preferably 20–50%. Additives such as dispersants, colorants, pigments polymers e.g. poly (ethylacrylat, methylmethacrylat), anti-tacking and antifoaming agents may also be included into the enteric coating layer(s). Other compounds may be added to increase film thickness and to decrease diffusion of acidic gastric juices into the acid susceptible material.

To protect the acid susceptible substance, the proton pump inhibitor, and to obtain an acceptable acid resistance of the dosage form according to the invention, the enteric coating layer(s) constitutes a thickness of approximately at least 10 $\mu$m, preferably more than 20 $\mu$m. The maximum thickness of the applied enteric coating is normally limited by processing conditions and the desired dissolution profile.

Alternatively, the enteric coating layer described above may also be used for enteric coating of conventional tablets comprising an acid susceptible proton pump inhibitor. Said enteric coating layered tablet is thereafter presscoated with antacid granules and pharmaceutical excipients.

Over-coating Layer

Pellets covered with enteric coating layer(s) may further be covered with one or more over-coating layer(s). The over-coating layer(s) should be water soluble or rapidly disintegrating in water. The over-coating layer(s) can be applied to the enteric coating layered pellets by coating or layering procedures in suitable equipments such as coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and others, used alone or in mixtures. Additives such as plasticizers, colorants, pigments, fillers, anti-tacking and anti-static agents, such for instance magnesium stearate, titaniumdioxide, talc and other additives may also be included into the over-coating layer(s). Said over-coating layer may further prevent potential agglomeration of enteric coating layered pellets, further protect the enteric coating layer towards cracking during the compaction process and enhance the tableting process. The maximum thickness of the applied over-coating layer(s) is normally limited by processing conditions and the desired dissolution profile.

The above described over-coating layer may also be used as a tablet filmcoating layer to obtain tablets of good appearance.

Antacid Agent(s) or Alginate Preparation

The active substance in form of one or more antacid agent(s) are dry mixed with inactive excipients such as fillers, binders, disintegrants, and other pharmaceutically acceptable additives. The mixture is wet massed with a granulation liquid. The wet mass is dried preferably to a loss on drying of less than 3% by weight. Thereafter the dry mass is milled to a suitable size for the granules, such as smaller than 4 mm, and preferably smaller than 1 mm. Suitable inactive excipients are for instance mannitol, corn starch, potato starch, low substituted hydroxypropylcellulose, microcrystalline cellulose and crosslinked polyvinylpyrrolidone. The dry mixture comprising antacid agent(s) is mixed with a suitable granulation liquid comprising for instance hydroxypropylcellulose or polyvinylpyrrolidone dissolved in purified water or alcohol or a mixture thereof.

Alternatively, the antacid agent(s) are dry mixed with pharmaceutically acceptable excipients according to the above. The alginate preparation should also be prepared by dry mixing with pharmaceutically acceptable excipients.

Multiple Unit Tablets

The enteric coating layered pellets comprising a proton pump inhibitor are mixed with the prepared antacid granules or with the prepared dry mixture comprising the antacid agent(s). The mixture is admixed with lubricant(s) and compressed into a multiple unit tableted dosage form. Suitable lubricants for the tableting process are for instance sodium stearyl fumarate, magnesium stearate and talc. The compressed tablet is optionally covered with a filmforming agent(s) to obtain a smooth surface of the tablet and further enhance the stability of the tablet during packaging and transport Such a coating layer may further comprise additives such as anti-tacking agents, colorants and pigments or other additives to obtain a tablet of good appearance.

Further, the different active substances may be formulated into different layers, wherein the layer comprising the proton pump inhibitor preferably is in the form of a multiple unit tableted dosage form layered with the prepared mixture of the antacid agent(s) or an alginate preparation. The two layers may be separated by a third layer comprising anti-tacking agents.

The fraction of enteric coating layered pellets constitutes less than 75% by weight of the total tablet weight and preferably less than 60%. By increasing the amount of the granules comprising the antacid agent(s) and excipients, the fraction of enteric coating layered pellets of the proton pump inhibitor may be reduced in the multiple unit tableted dosage form. By choosing small enteric coating layered pellets in the formulation according to the present invention, the number of pellets in each tablet can be held high which in turn makes the tablet divisible with retained dosing accuracy.

Thus, the preferred multiple unit tablet formulation consists of enteric coating layered pellets containing the acid susceptible proton pump inhibitor, optionally in admixture with alkaline reacting compound(s), compressed into tablets together with the prepared antacid mixture and optionally tablet excipients. The addition of an alkaline reacting material to the proton pump inhibitor is not necessary, in any sense, but such a substance may further enhance the stability of the proton pump inhibitor or some of the alkaline reacting compounds may react in situ with the enteric coating material to form a separating layer. The enteric coating layer(s) is making the pellets of the dosage form insoluble in acidic media, but disintegrating/dissolving in near neutral to alkane media such as, for instance the liquids present in the proximal part of the small intestine, where dissolution of the proton pump inhibitor is desired. The enteric coating layered pellets may further be covered with an overcoating layer before being formulated into the tablet and they may also contain one or more separating layer(s) in between the core material and the enteric coating layer(s).

Process

The process for the manufacture of the dosage form represents a further aspect of the invention. After formulation of the pellets by spray coating or layering of the proton pump inhibitor onto seeds, or by extrusion/spheronization or granulation, e.g. rotor granulation of homogeneous pellets, the pellets are first optionally covered with the separating layer(s) and then with the enteric coating layer(s) or a separating layer is spontaneously developed in situ between the core material and the enteric coating layer material. The coating is carried out as described above and in the accompanying examples. The preparation of the antacid mixture is also described above and in the examples. The pharmaceutical processes can preferably be completely water-based.

The enteric coating layered pellets, with or without an over-coat, are mixed with the prepared antacid granules, tablet excipients and other pharmaceutically acceptable additives and compressed into tablets. Alternatively, the enteric coating layered pellets may be intimately mixed with tablet excipients and precompressed and further layered with the antacid or alginate preparation and finally compressed into a tablet. As a further alternative the proton pump inhibitor in form of a powder may be mixed with tablet excipients and compressed into a tablet which is optionally layered with a separating layer and thereafter enteric coating layered. Said tablet core is then presscoated with the antacid preparation. Finally the tablet may be covered by a tablet coat.

As a further alternative, the proton pump inhibitor in the form of enteric coating layered pellets may be filled in a sachet together with an alginate optionally mixed with excipients.

Use of the Preparation

The dosage forms according to the invention are especially advantageous in the treatment of dyspepsia and other gastrointestinal disorder to provide an immediate symptom relief and a long-lasting symptom resolution. The dosage forms are administered one to several times a day, preferably once or twice daily. The typical daily dose of the active substances varies and will depend on various factors such as the individual requirements of the patients, the mode of administration and disease. In general each dosage form will comprise 0.1–200 mg of the proton pump inhibitor and 0.1–1000 mg of the antacid agent(s)/alginate. Preferably, each dosage form will comprise 5–80 mg of the proton pump inhibitor and 100–900 mg of the antacid agent(s)/alginate, and more preferably 10–40 mg of proton pump inhibitor and 250–650 mg of the antacid agent(s)/alginate, respectively.

The multiple unit tablet preparation is also suitable for dispersion in an aqueous liquid with slightly acidic pH-value before being orally administered or fed through a nasogastric tube.

The invention is illustrated more in detail in the following examples.

EXAMPLES

Example 1

Multiple unit tableted dosage form comprising magnesium omeprazole and antacid agents (batch size 400 tablets).

| Core material | |
| --- | --- |
| Magnesium omeprazole | 5.0 kg |
| Sugar sphere seeds | 10.0 kg |
| Hydroxypropyl methylcellulose | 0.75 kg |
| Water purified | 20.7 kg |
| Separating layer | |
| Core material (acc. to above) | 10.2 kg |
| Hydroxypropyl cellulose | 1.02 kg |
| Talc | 1.75 kg |
| Magnesium stearate | 0.146 kg |
| Water purified | 21.4 kg |
| Enteric coating layer | |
| Pellets covered with separating layer (acc. to above) | 11.9 kg |
| Methacrylic acid copolymer (30% suspension) | 19.8 kg |
| Triethyl citrate | 1.79 kg |

| -continued | |
| --- | --- |
| Mono- and diglycerides (NF) | 0.297 kg |
| Polysorbate 80 | 0.03 kg |
| Water purified | 11.64 kg |
| Over-coating layer | |
| Enteric coating layered pellets (acc. to above) | 20.0 kg |
| Hydroxypropyl methylcellulose | 0.238 kg |
| Magnesium stearate | 0.007 kg |
| Water purified | 6.56 kg |
| Tablets | |
| Prepared pellets comprising omeprazole Mg-salt (acc. to above) | 31.3 g |
| Microcrystalline cellulose | 140.0 g |
| Calcium carbonate | 100.0 g |
| Aluminium hydroxide/magnesium carbonate | 100.0 g |
| Potato starch | 46.4 g |
| Water purified | 314 g |
| Polyvidone crosslinked | 38.0 g |
| Sodium stearyl fumarate | 4.6 g |

Suspension layering was performed in a fluid bed apparatus. Magnesium omeprazole was sprayed onto sugar sphere seeds from a water suspension containing the dissolved binder. The size of sugar sphere seeds were in the range of 0.25 to 0.35 mm.

The prepared core material was covered with a separating layer of a hydroxypropyl cellulose solution containing talc and magnesium stearate. The enteric coating layer consisting of methacrylic acid copolymer, mono- and diglycerides, triethyl citrate and polysorbate was sprayed onto the pellets covered with a separating layer in a fluid bed apparatus. In a fluid bed apparatus enteric coating layered pellets were coated with a hydroxypropyl methylcellulose containing magnesium stearate. The over-coating layered pellets were classified by sieving.

A small amount of the potato starch was dissolved in purified hot water to form the granulation liquid. Calcium carbonate, aluminium hydroxide/magnesium carbonate, potato starch and microcrystalline cellulose are dry-mixed. The granulation liquid was added to the dry mixture and the mass was wet-mixed. The wet mass was dried in a steam-oven at 50° C. The prepared granulation was milled through sieve 1 mm in an oscillating mill equipment.

The enteric coating layered pellets with an over-coating layer, prepared granules, polyvidone crosslinked and sodium stearyl fumarate were mixed and compressed into tablets using a tableting machine equipped with 9×20 mm oval punches. The amount of omeprazole in each tablet was approx. 10 mg and the amount of antacid agents were approx. 500 mg in total. Tablet hardness was measured to 110N.

Optionally the obtained tablets were covered with a tablet coating layer.

Results

| | "Acid resistance" i.e. % left after exposure to 0.1N HCl for 2 hrs |
| --- | --- |
| | Tablets |
| Ex 1 | 93% |

Example 2

Multiple unit tableted dosage form comprising magnesium omeprazole and antacid agents (batch size 500 tablets).

| Core material | |
|---|---|
| Magnesium omeprazole | 10.0 kg |
| Sugar sphere seeds | 10.0 kg |
| Hydroxypropyl methylcellulose | 1.5 kg |
| Water purified | 29.9 kg |
| Separating layer | |
| Core material (acc. to above) | 20.0 kg |
| Hydroxypropyl cellulose | 2.0 kg |
| Talc | 3.43 kg |
| Magnesium stearate | 0.287 kg |
| Water purified | 41.0 kg |
| Enteric coating layer | |
| Pellets covered with separating layer (acc. to above) | 24.5 kg |
| Methacrylic acid copolymer (30% suspension) | 32.7 kg |
| Triethyl citrate | 2.94 kg |
| Mono- and diglycerides (NF) | 0.49 kg |
| Polysorbate 80 | 0.049 kg |
| Water purified | 19.19 kg |
| Over-coating layer | |
| Enteric coating layered pellets (acc. to above) | 37.8 kg |
| Hydroxypropyl methylcellulose | 0.49 kg |
| Magnesium stearate | 0.0245 kg |
| Water purified | 11.6 kg |
| Tablets | |
| Prepared pellets comprising magnesium omeprazole (acc. to above) | 47.45 g |
| Calcium carbonate | 123.9 g |
| Magnesium hydroxide | 123.9 g |
| Potato starch | 52.2 g |
| Water purified | 435 g |
| Microcrystalline cellulose | 175 g |
| Polyvidone crosslinked | 50 g |
| Sodium stearyl fumarate | 6.0 g |

Enteric coating layered pellets of magnesium omeprazole with an overcoating layer were prepared as in Example 1.

A small amount of the potato starch was dissolved in hot purified water to form the granulation liquid. Calcium carbonate, magnesium hydroxide and potato starch were dry-mixed. The granulation liquid was added to the dry mixture and the mass was wet-mixed. The wet mass was dried in a steamoven at 40° C. The prepared granulation was milled through sieve 1 mm in an oscillating mill equipment.

The enteric coated layered pellets with an over-coating layer, prepared granules, microcrystalline cellulose, polyvidone crosslinked and sodium stearyl fumarate were mixed and compressed into tablets using a tableting machine equipped with 9×20 mm oval punches. The amount of omeprazole in each tablet was approx. 20 mg and the amount of antacid agents were approx. 500 mg in total. Tablet hardness was measured to 30–40N.

Optionally the obtained tablets were covered with a tablet coating layer.

Example 3

Multiple unit tableted dosage form comprising S-omeprazole magnesium salt and antacid agents (batch size 500 tablets).

| Core material | |
|---|---|
| S-omeprazole magnesium salt | 120 g |
| Sugar sphere seeds | 150 g |
| Hydroxypropyl methylcellulose | 18 g |
| Polysorbate 80 | 2.4 g |
| Water purified | 562 g |
| Separating layer | |
| Core material (acc. to above) | 200 g |
| Hydroxypropyl cellulose | 30 g |
| Talc | 51.4 g |
| Magnesium stearate | 4.3 g |
| Water purified | 600 g |
| Enteric coating layer | |
| Pellets covered with separating layer (acc. to above) | 250 g |
| Methacrylic acid copolymer (30% suspension) | 333.7 g |
| Triethyl citrate | 30 g |
| Mono- and diglycerides (NF) | 5 g |
| Polysorbate 80 | 0.5 g |
| Water purified | 196 g |
| Tablets | |
| Prepared pellets comprising (s)-omeprazole Mg-salt | 63.7 g |
| Calcium carbonate | 123.9 g |
| Magnesium hydroxide | 123.9 g |
| Potato starch | 52.2 g |
| Water purified | 435 g |
| Microcrystalline cellulose | 175 g |
| Polyvidone crosslinked | 50.0 g |
| Sodium stearyl fumarate | 6.0 g |

Suspension layering was performed in a fluid bed apparatus. S-omeprazole magnesium salt was sprayed onto sugar sphere seeds from a water suspension containing the dissolved binder and polysorbate 80. The size of sugar sphere seeds were in the range of 0.25 to 0.35 mm.

The prepared core material was covered with a separating layer in a fluid bed apparatus with hydroxypropyl cellulose solution containing talc and magnesium stearate. The enteric coating layer consisting of methacrylic acid copolymer, mono-and diglycerides, triethyl citrate and polysorbate was sprayed onto the pellets covered with a separating layer in a fluid bed apparatus. The enteric coating layered pellets were classified by sieving.

A small amount of the potato starch was dissolved in hot purified water to form the granulation liquid. Calcium carbonate, magnesium hydroxide and potato starch were dry-mixed. The granulation liquid was added to the dry mixture and the mass was wet-mixed.

The wet mass was dried in a steamoven at 40° C. The prepared granulation was milled through sieve 1 mm in an oscillating mill equipment.

The enteric coating layered pellets, prepared granules, polyvidone crosslinked, microcrystalline cellulose and sodium stearyl fumarate were mixed and compressed into tablets using a tableting machine equipped with 9×20 mm oval punches. The amount of S-omeprazole in each tablet was approx. 20 mg and the amount of antacid agents were approx. 500 mg in total. Tablet hardness was measured to 30N.

Optionally the obtained tablets were covered with a tablet coating layer.

Example 4

Three-layered tableted dosage form with a fast disintegrating layer comprising omeprazole, a separating layer and a layer comprising alginic acid. (batch size 1,000 tablets)

Tablets

| | |
|---|---:|
| First tablet layer | |
| Alginic acid | 500 g |
| Sodium hydrogencarbonate | 150 g |
| Microcrystalline cellulose | 87 g |
| Polyvinyl pyrrolidone crosslinked | 13 g |
| Sodium stearyl fumarate | 3.8 g |
| Separating layer | |
| Microcrystalline cellulose | 80 g |
| Second tablet layer | |
| Enteric coating layered pellets comprising omeprazole Mg-salt (manufacturing and composition as in example 1) | 78.3 g |
| Microcrystalline cellulose | 174 g |
| Polyvinyl pyrrolidone crosslinked | 26 g |
| Sodium stearyl fumarate | 1.4 g |

Alginic acid, sodium hydrogencarbonate, microcrystalline cellulose, polyvinyl pyrrolidone and sodium stearyl fumarate were dry-mixed and precompressed as a first layer in a tableting machine equipped with 10×21 mm oval punches. Microcrystalline cellulose was filled on top of the first layer to form a separating layer to the next layer.

The enteric coating layered pellets, microcrystalline cellulose, polyvinyl pyrrolidone and sodium stearyl fumarate were dry-mixed and filled on top of the separating layer. The three layers were compressed into a three layers tablet.

Optionally the tablet was covered by a tablet coating layer.

The amount of omeprazole in each tablet is approx. 10 mg and the amount of alginic acid was approx 500 mg.

The best mode to practise the invention is described in Examples 1 and 4.

The enteric coating layered pellets comprising a proton pump inhibitor may also be prepared as described in the following examples.

Example 5

Preparation of enteric coating layered pellets by extrusion/spheronization.

| | |
|---|---:|
| Core material | |
| Magnesium omeprazole | 600 g |
| Mannitol | 1000 g |
| Microcrystalline cellulose | 300 g |
| Hydroxypropyl cellulose | 100 g |
| Sodium lauryl sulphate | 6 g |
| Water purified | 802 g |
| Separating layer | |
| Core material | 400 g |
| Hydroxypropyl methylcellulose | 48 g |
| Water purified | 960 g |
| Enteric coating layer | |
| Pellets covered with separating layer | 200 g |
| Methacrylic acid copolymer | 100 g |
| Triethyl citrate | 30 g |
| Mono- and diglycerides (NF) | 5 g |
| Polysorbate 80 | 0.5 g |
| Water purified | 309 g |

Sodium lauryl sulphate is dissolved in purified water to form the granulation liquid. Magnesium omeprazole, mannitol, microcrystalline cellulose and hydroxypropyl cellulose are dry-mixed. The granulation liquid is added to the powder mixture and the mass is wet-mixed. The wet mass is forced through an extruder equipped with screens of size 0.5 mm. The extrudate is spheronized on a friction plate in a spheronizing apparatus. The core material is dried in a fluid bed dryer and classified. The prepared core material is covered by a separating layer in a fluid bed apparatus with a hydroxypropyl methylcellulose/water solution.

The enteric coating layer is applied to the pellets covered with separating layer from an aqueous dispersion of methacrylic acid copolymer plasticized with triethyl citrate to which a mono- and diglycerides/polysorbate dispersion has been added. The pellets are dried in a fluid bed apparatus.

Example 6

Preparation of enteric coating layered pellets by powder layering of sugar sphere seeds.

| | |
|---|---:|
| Core material | |
| Magnesium omeprazole | 1500 g |
| Sugar sphere seeds | 1500 g |
| Hydroxypropyl methylcellulose | 420 g |
| Aerosil® | 8 g |
| Water purified | 4230 g |
| Separating layer | |
| Core material | 500 g |
| Hydroxypropyl cellulose | 40 g |
| Talc | 67 g |
| Magnesium stearate | 6 g |
| Water purified | 800 g |
| Enteric coating layer | |
| Pellets covered with separating layer | 500 g |
| Methacrylic acid copolymer | 200 g |
| Triethyl citrate | 60 g |
| Water purified | 392 g |

Magnesium omeprazole, part of the hydroxypropyl methylcellulose and Aerosil® are dry-mixed forming a powder. Sugar sphere seeds (0.25–0.40 mm) are layered with the powder in a centrifugal fluidized coating granulator while spraying a hydroxypropyl methylcellulose solution (6%, w/w).

The prepared core material is dried and covered by a separating layer in a centrifugal fluidized coating-granulator. A fluid bed apparatus is used for enteric coating layereing.

Example 7

Preparation of enteric coating layered pellets with cores of silicon dioxide seeds.

| | |
|---|---:|
| Core material | |
| Magnesium omeprazole | 8.00 kg |
| Silicon dioxide | 8.00 kg |
| Hydroxypropyl methylcellulose | 1.41 kg |
| Sodium lauryl sulphate | 0.08 kg |
| Water purified | 28.00 kg |
| Separating layer | |
| Core material (acc. to above) | 10.00 kg |
| Hydroxypropyl methylcellulose | 0.80 kg |
| Water purified | 10.00 kg |

| Enteric coating layer | |
|---|---|
| Pellets covered with separating layer (acc. to above) | 300 g |
| Methacrylic acid copolymer | 124 g |
| Polyethylene glycol 400 | 25 g |
| Mono- and diglycerides (NF) | 3 g |
| Polysorbate 80 | 1 g |
| Water purified | 463 g |

Suspension layering is performed in a fluid bed apparatus. Magnesium omeprazole is sprayed onto the silicon dioxide seeds from a water suspension containing the dissolved binder and a surface active ingredient.

The prepared core material is covered with a separating layer in a fluid bed apparatus with a hydroxypropyl methylcellulose solution. The enteric coating layer consisting of methacrylic acid copolymer, mono- and diglycerides, polyethylene glycol 400 and polysorbate is sprayed onto the pellets covered with separating layer in a fluid bed apparatus.

Example 8

Preparation of enteric coating layered pellets.

| Enteric coating layer | |
|---|---|
| Pellets covered with separating layer (manufacturing and composition as in example 10) | 500 g |
| Methacrylic acid copolymer | 250 g |
| Polyethylene glycol 6000 | 75 g |
| Mono- and diglycerides (NF) | 12.5 g |
| Polysorbate 80 | 1.2 g |
| Water purified | 490 g |

Example 9

Preparation of enteric coating layered pellets.

| Enteric coating | |
|---|---|
| Pellets covered with separating layer (manufacturing and composition as in example 1) | 500 g |
| Hydroxypropyl methylcellulose phthalate | 250 g |
| Cetanol | 50 g |
| Ethanol (95%) | 1000 g |
| Acetone | 2500 g |

Example 10

Preparation of enteric coating layered pellets.

| Core material | |
|---|---|
| Omeprazole | 225 g |
| Mannitol | 1425 g |
| Hydroxypropyl cellulose | 60 g |
| Microcrystalline cellulose | 40 g |
| Lactose anhydrous | 80 g |
| Sodium lauryl sulphate | 5 g |
| Disodium hydrogen phosphate dihydrate | 8 g |

| | |
|---|---|
| Water purified | 350 g |
| Separating layer | |
| Core material | 300 g |
| Hydroxypropyl cellulose | 30 g |
| Talc | 51 g |
| Magnesium stearate | 4 g |
| Enteric coating layer | |
| Pellets covered with separating layer | 300 g |
| Methacrylic acid copolymer | 140 g |
| Triethyl citrate | 42 g |
| Mono- and diglycerides (NF) | 7 g |
| Polysorbate 80 | 0.7 g |

The dry ingredients for producing the core material are well mixed in a mixer. Addition of granulation liquid is made and the mixture is kneaded and granulated to a proper consistency. The wet mass is pressed through an extruder screen and the granules are converted into a spherical form in a spheronizer. The core material is dried in a fluid bed apparatus and classified into a suitable particle size range, e.g. 0.5–1.0 mm. The prepared core material is covered with a separating layer and enteric coating layered as described in previous examples.

Preparation of active substance.

Magnesium omeprazole used in some of the examples is produced according to the process described in WO95/01977, the single enantiomers of omeprazole salts are prepared as described in WO94/27988 and omeprazole is produced according to the process disclosed in EP-A1 0005129. These documents are hereby incorporated in a whole by reference.

What is claimed is:

1. An oral pharmaceutical composition comprising, as a first component, an acid susceptible proton pump inhibitor, and as a separate second component, at least one substance selected from the group consisting of antacid agents, alginates and mixtures thereof, and as an optional third component, pharmaceutically acceptable excipients, wherein:
   (a) the composition is in the form of a multiple unit tablet;
   (b) the first component is in the form of pellets covered with an enteric coating layer,
   (c) the second component is separated from the first component by the enteric coating layer covering the first component; and
   (d) the enteric coating layer has mechanical properties such that the acid resistance of the enteric coated pellets is not significantly affected by compression of the pellets with the other tablet components during tableting.

2. A process for the manufacture of a composition in the form of a multiple unit tableted dosage form having separate layers and comprising, as a first component in one layer, an acid susceptible proton pump inhibitor, and as a second component in a separate second layer, at least one substance selected from the group consisting of antacid agents, alginates and mixtures thereof, wherein the process comprises the steps of:
   (a) preparing the proton pump inhibitor in the form of enteric coating layered pellets;
   (b) mixing the enteric coated pellets with pharmaceutically acceptable excipients;
   (c) precompressing and further providing the mixture with the second layer; and (d) compressing the layered mixture into a tablet.

3. A process for the manufacture of a composition in the form of a multiple unit tableted dosage form comprising, as a first component, an acid susceptible proton pump inhibitor, and as a separate second component, at least one substance selected from the group consisting of antacid agents, alginates and mixtures thereof, wherein the process comprises the steps of:

(a) preparing the proton pump inhibitor in the form of enteric coating layered pellets;

(b) mixing the enteric coated pellets with the second component; and (c) compressing the dry mixture into a multiple unit tablet without affecting any significant change of the acid resistance of the enteric coating layer.

4. The composition according to claim 1, wherein the proton pump inhibitor is covered by a separating layer located underneath the enteric coating layer.

5. The composition according to claim 1, wherein the tableted dosage form comprises an acid susceptible proton pump inhibitor and two antacid agents.

6. The composition according to claim 1, wherein the proton pump inhibitor is omeprazole, an alkaline salt of omeprazole, a single enantiomer of omeprazole or an alkaline salt of the single enantiomer.

7. The composition according to claim 6, wherein the proton pump inhibitor is S-omeprazole magnesium salt.

8. The composition according to claim 1, wherein the proton pump inhibitor is lansoprazole, an alkaline salt of lansoprazole, a single enantiomer of lansoprazole or an alkaline salt of the single enantiomer.

9. The composition according to any one of claims 6–8, wherein the antacid agents are aluminum hydroxide in combination with magnesium or aluminum carbonate.

10. The composition according to any one of claims 6–8, wherein the antacid agents are calcium hydroxide in combination with magnesium or calcium carbonate.

11. The composition according to claim 1, wherein the amount of the proton pump inhibitor is in the range of 5–80 mg, and the amount of the second component is in the range of 100–900 mg.

12. The composition according to claim 1, wherein the amount of the proton pump inhibitor is in the range of 10–40 mg, and the amount of the second component is in the range of 250–650 mg.

13. The composition according to claim 1, wherein the tableted dosage form comprises a first layer comprising the proton pump inhibitor and a separate second layer comprising the second component.

14. A method for the treatment of disorders associated with dyspepsia in mammals and man by administering to a host in need thereof a therapeutically effective dose of a multiple unit tableted dosage form according to claim 1.

15. The composition according to claim 1, wherein the acid resistance of the enteric coating layered pellets is in compliance with the requirements on enteric coating layered articles defined in the United States Pharmacopeia.

16. The composition according to claim 1, wherein the acid resistance of the enteric coating layered pellets does not decrease more than 10% upon the tableting of the pellets into the multiple unit tableted dosage form.

17. The composition according to claim 1, wherein the enteric coating layered pellets comprises a plasticized enteric coating layer material.

18. The composition according to claim 1, wherein the enteric coating layered pellets are further covered with an over-coating layer comprising pharmaceutically acceptable excipients.

19. The composition according to claim 1, wherein the tablet is divisible.

20. The composition according to claim 19, wherein the tablet is dispersible to form an aqueous suspension comprising the second component and the enteric coating layered pellets comprising a proton pump inhibitor.

21. A method according to claim 14, wherein the disorder is a gastric disorder associated with heartburn.

22. The composition according to claim 1, wherein the proton pump inhibitor is in the form of a multiple unit tableted dosage form layered with a coating layer comprising the second component.

23. The composition according to claim 1, wherein the proton pump inhibitor is selected from the group consisting of the racemic form and a single enantiomer of each of omeprazole, lansoprazole, pantoprazole, pariprazole, and pharmaceutically acceptable salts of the racemic forms and of the single enantiomers.

24. The process according to claims 3, which further comprises the step of admixing a pharmaceutically acceptable excipient to the tablet mixture of step (b).

25. The process according to claim 3, further comprising the step of: covering the proton pump inhibitor with a separating layer before applying the enteric coating layer.

26. The composition according to claim 1, wherein the second component is a mixture of an antacid and alginate.

27. The composition according to any one of claims 6–8, wherein the antacid agents are magnesium hydroxide in combination with aluminum carbonate, magnesium carbonate or calcium carbonate.

* * * * *